(12) United States Patent
Emoto et al.

(10) Patent No.: US 10,119,904 B2
(45) Date of Patent: Nov. 6, 2018

(54) BIREFRINGENCE MEASUREMENT DEVICE AND BIREFRINGENCE MEASUREMENT METHOD

(71) Applicant: NATIONAL INSTITUTE OF ADVANCED INDUSTRIAL SCIENCE AND TECHNOLOGY, Tokyo (JP)

(72) Inventors: Akira Emoto, Kyoto (JP); Naoki Otani, Kyoto (JP); Takashi Fukuda, Ibaraki (JP)

(73) Assignee: National Institute of Advanced Industrial Science, Tokyo (JP)

( * ) Notice: Subject to any disclaimer, the term of this patent is extended or adjusted under 35 U.S.C. 154(b) by 0 days.

(21) Appl. No.: 15/505,621

(22) PCT Filed: Aug. 11, 2015

(86) PCT No.: PCT/JP2015/072783
§ 371 (c)(1),
(2) Date: Feb. 22, 2017

(87) PCT Pub. No.: WO2016/031567
PCT Pub. Date: Mar. 3, 2016

(65) Prior Publication Data
US 2017/0276597 A1    Sep. 28, 2017

(30) Foreign Application Priority Data

Aug. 26, 2014  (JP) .................................. 2014-171159

(51) Int. Cl.
*G01N 21/23*    (2006.01)
(52) U.S. Cl.
CPC ..... *G01N 21/23* (2013.01); *G01N 2201/0683* (2013.01)

(58) Field of Classification Search
CPC .................................. G01N 21/23; G01J 4/00
(Continued)

(56) References Cited

U.S. PATENT DOCUMENTS

2010/0020168 A1\*  1/2010  Ye ......................... G01N 21/21
                                                                348/92

FOREIGN PATENT DOCUMENTS

EP          1429128        6/2004
JP          58-087445      5/1983
(Continued)

OTHER PUBLICATIONS

Ono, Hiroshi et al., Diffraction Properties in Polarization Holography Written by Elliptical Polarized Light, Japanese Journal of Applied Physics, vol. 49, pp. 032502-1 through 032502-4, 2010.
(Continued)

*Primary Examiner* — Roy M Punnoose
(74) *Attorney, Agent, or Firm* — Kirchstein, Israel, Schiffmiller & Pieroni, P.C.

(57) ABSTRACT

A birefringence measurement device includes a light flux generator for generating light flux, a light flux irradiator for irradiating a measurement target with the light flux in a predetermined polarization state, an imaging optical system for forming an image from light flux transmitted through the measurement target, a polarization/diffraction grating positioned within the imaging optical system, an image pickup for generating a light-dark signal related to brightness of the image, and an output for outputting information regarding a phase difference for the light flux. The phase difference resulting from the transmission through the measurement target is determined on the basis of the light-dark signal. The image pickup generates the light-dark signal for the image based on at least one beam of diffracted light from among a plurality of beams of diffracted light produced by the grat-
(Continued)

ing. A two-dimensional distribution of birefringence is obtained in real time without a rotating mechanism.

10 Claims, 14 Drawing Sheets

(58) Field of Classification Search
USPC .......................................................... 356/365
See application file for complete search history.

(56) References Cited

FOREIGN PATENT DOCUMENTS

| JP | 2005-257508 | 9/2005 |
| JP | 2006-071458 | 3/2006 |
| JP | 2007-085607 | 10/2007 |

OTHER PUBLICATIONS

Emoto, Akira et al., Form Birefringence in Intrinsic Birefringement Media Possessing A Subwavelength Structure, Applied Optics, vol. 49, No. 23, pp. 4355-4361, Aug. 10, 2010.
International Search Report in PCT/JP2015/072783, dated Sep. 29, 2015.
Gorodetski et al. Space-Variant Polarization Manipulation for Far-Field Polarimetry by Use of Subwavelength Dielectric Gratings, Optics Letters, vol. 30, No. 17, pp. 2245-2247, Sep. 1, 2005.
Biener et al., Near-Field Fourier Transform Polarimetry by Use of a Discrete Space-Variant Subwavelength Grating, Journal of the Optical Society of America, vol. 20, No. 10, pp. 1940-1948, Oct. 1, 2003.
Supplementary European Search Report in corresponding EP Patent Application No. 15835242, dated Mar. 26, 2018.
Vartiainen et al., Surface-Relief Polarization Gratings for Visible Light, Optics Express, vol. 18, No. 22, pp. 22850-22858, Oct. 25, 2010.

* cited by examiner (A)

(B)

(C)

(A)

(B)

1mm (A)

(B)

(C)

(D)

(B) 10 Lines/mm (EQUIVALENT TO RESOLUTION OF 50 μm)

(C) 20 Lines/mm (EQUIVALENT TO RESOLUTION OF 25 μm)

(D) 40 Lines/mm (EQUIVALENT TO RESOLUTION OF 12.5 μm)

(A)

(B)

Prior Art

Prior Art

BIREFRINGENCE MEASUREMENT DEVICE AND BIREFRINGENCE MEASUREMENT METHOD

TECHNICAL FIELD

The present invention relates to a birefringence measurement device and method for measuring birefringence in a birefringent medium.

BACKGROUND ART

As an approach to measuring birefringence in a birefringent medium, the crossed-Nicol method is well known. In this approach, a combination of a polarizer and an analyzer, which are perpendicular to each other, and a birefringent medium, which is disposed therebetween as a measurement target, are rotated relative to each other, and during the rotation, the intensity $I_{out}(\theta)$ of light transmitted through the polarizer, the measurement target, and the analyzer is measured, and birefringence Δn in the measurement target is determined by the following equation.

$$I_{out}(\theta) = I_{in}\sin^2\left(\frac{\pi}{\lambda}\Delta nd\right)\sin^2(2\theta) \qquad [\text{Equation 1}]$$

Here, $I_{in}$ is the intensity of light incident from the polarizer, θ is the relative rotation angle of the measurement target, and d is the thickness of the measurement target. Moreover, Δnd, which is represented by the product of the birefringence Δn and the thickness d, is the optical path difference between extraordinary and ordinary components of light with a wavelength λ passing through the measurement target, and the optical path difference causes a phase difference δ.

$$\delta = \frac{2\pi}{\lambda}\Delta nd \qquad [\text{Equation 2}]$$

In this manner, the birefringence Δn is derived from the phase difference δ of the light having passed through the measurement target with the thickness d, and therefore, birefringence measurement is synonymous with phase difference measurement, and in some cases, might be referred to as birefringent phase difference measurement.

However, this approach requires the combination of the polarizer and the analyzer and the measurement target to be rotated at least 180° relative to each other, resulting in issues of time-consuming measurement and necessity for a extensive rotating mechanism. Accordingly, there has been proposed a rotating analyzer method in which the polarizer creates circularly polarized light to be incident on the measurement target and only the analyzer at the end is rotated, but such a method still requires a rotating mechanism.

To overcome the issues, there have been proposed various approaches which require no rotating mechanism. For example, Patent Document 1 proposes a birefringence measurement device 100 (see FIG. 15) including a means for irradiating a measurement target 20 with polarized light L10, beam splitters 101 and 102 for dividing polarized light L11 transmitted through the measurement target 20 in three components, analyzers 103, 104, and 105 for allowing the three components of the divided polarized light L11, which oscillate in specific directions, to pass therethrough, optical detectors 106, 107, and 108 for measuring the intensities of the light transmitted through the analyzers 103, 104, and 105, and an arithmetic device 109, such as a computer, for determining an elliptical trajectory of the polarized light L11 on the basis of the results obtained by the optical detectors 106, 107, and 108. In the birefringence measurement device 100, the analyzers 103 and 104 differ in angle by 45°, and the analyzers 103 and 105 differ in angle by 90°.

The birefringence measurement device 100 makes it possible to determine birefringence Δn in the measurement target 20 on the basis of the relationship between a known polarization state of the polarized light L0 and a polarization state of the polarized light L11 determined by the arithmetic device 109.

Furthermore, Patent Document 2 proposes a birefringence measurement device 200 (see FIG. 16) in which a measurement target 20 is irradiated with light flux having a known polarization state (e.g., circularly polarized light L20) and a polarization state of transmitted light L21 is detected by a polarizer array 201 and an area sensor 202 (e.g., a CMOS camera). As shown in (B) of FIG. 16, the polarizer array 201 includes a plurality of polarizer units 203 in series both in X and Y directions, and each polarizer unit 203 includes 4×4 (=16) polarizers different in transmission axis from one another.

In the birefringence measurement device 200, when compared to the birefringence measurement device 100, the polarizer array 201 plays the same role as the analyzers 103, 104, and 105, and the area sensor 202 plays the same role as the optical detectors 106, 107, and 108. Moreover, the birefringence measurement device 200 does not require the beam splitters 101 and 102 as does the birefringence measurement device 100. Accordingly, the birefringence measurement device 200 makes it possible to measure a two-dimensional distribution of birefringence Δn in the measurement target 20 by a simpler configuration than the configuration of the birefringence measurement device 100.

PRIOR ART DOCUMENTS

Patent Documents

Patent Document 1: Japanese Laid-Open Patent Publication No. 2006-71458
Patent Document 2: Japanese Laid-Open Patent Publication No. 2007-263593

Non-Patent Document

Non-Patent Document 1: Akira Emoto, Masaya Nishi, Makoto Okada, Sayaka Manabe, Shinji Matsui, Nobuhiro Kawatsuki, and Hiroshi Ono, "Form birefringence in intrinsic birefringent media possessing a subwavelength structure", APPLIED OPTICS, 10 Aug. 2010, Vol. 49, No. 23, pp. 4355-4361

DISCLOSURE OF THE INVENTION

Problems to be Solved by the Invention

However, in the conventional birefringence measurement device 100, the arithmetic device 109 performs a two-phase calculation process (i.e., calculation of ellipticity by an elliptic function based on the intensities of the light detected by the optical detectors 106, 107, and 108 and calculation of the phase difference δ and the birefringence Δn), and therefore, even if a high-performance arithmetic device 109 is provided, it is still difficult to measure in real time the birefringence Δn, which changes constantly. Moreover, in the case of measuring a two-dimensional distribution of birefringence Δn in a somewhat wide area of the measurement target 20, in other words, a two-dimensional distribution of a phase difference δ due to the measurement target 20, the conventional birefringence measurement device 100 requires light intensity distributions determined by the optical detectors 106, 107, and 108 to be accurately aligned with one another before the arithmetic device 109 determines the phase difference δ resulting in a large and complicated device.

Moreover, as for the conventional birefringence measurement device 200, the polarization state of the transmitted light L21 is measured by the entire polarizer unit 203 rather than each polarizer included in the polarizer unit 203, so that birefringence Δn in microscopic regions of the measurement target 20 that correspond to the individual polarizers cannot be measured microscopically. That is, there is an issue where the birefringence measurement device 200 is unsuitable for measuring in detail a two-dimensional distribution of birefringence Δn.

The present invention has been achieved under the above circumstances, with a problem thereof being to provide a birefringence measurement device and method capable of measuring a two-dimensional distribution of birefringence in a measurement target in real time and in detail using a simple configuration without a rotating mechanism.

Solution to the Problems

To solve the above problem, the present invention provides a birefringence measurement device including light flux generating means for generating light flux, light flux irradiating means for irradiating a measurement target with the light flux in a predetermined polarization state, an imaging optical system for forming an image from light flux transmitted through the measurement target, a polarization/diffraction grating disposed in a position within the imaging optical system, image pickup means for generating a light-dark signal related to brightness of the image formed by the imaging optical system, and output means for outputting information regarding a phase difference for the light flux transmitted through the measurement target, the phase difference resulting from the transmission through the measurement target and being determined on the basis of the light-dark signal, in which the image pickup means generates the light-dark signal for an image based on at least one of a plurality of beams of diffracted light produced by the polarization/diffraction grating.

In the birefringence measurement device, the light flux incident on the measurement target is, for example, circularly polarized light. In this case, more preferably, the image pickup means generates the light-dark signal for an image based on the beam of diffracted light produced by the polarization/diffraction grating, the beam being either +1- or −1-order diffracted light and becoming darkest when the light flux transmitted through the measurement target has the same circular polarization as circularly polarized light incident on the measurement target and becoming brightest when the light flux transmitted through the measurement target has opposite circular polarization to the circularly polarized light incident on the measurement target.

In the birefringence measurement device, the polarization/diffraction grating is a form birefringence/polarization/diffraction grating made from, for example, a quartz plate or a transparent resin plate. The polarization/diffraction grating includes, for example, a plurality of grating units arranged in an adjacency direction, each of the grating units is a one-dimensional strip grating, and each adjacent pair of the grating units differs in grating vector orientation so as to form a periodic structure in the adjacency direction. In this case, preferably, the cycle of the strip gratings is shorter than 0.6 times the wavelength of the light flux generated by the light flux generating means.

In the birefringence measurement device, the imaging optical system is a 4f optical system. In this case, the polarization/diffraction grating may be disposed halfway between the measurement target and the image pickup means.

To solve the above problem, the present invention also provides a birefringence measurement method including a light flux generating step for generating light flux, a light flux irradiating step for irradiating a measurement target with the light flux in a predetermined polarization state, an image forming step for forming an image from light flux transmitted through the measurement target by means of a polarization/diffraction grating, a signal generating step for generating a light-dark signal related to brightness of the image formed in the image forming step, and an output step for outputting information regarding a phase difference for the light flux transmitted through the measurement target, the phase difference resulting from the transmission through the measurement target and being determined on the basis of the light-dark signal, in which, in the signal generating step, the light-dark signal is generated for an image based on at least one of a plurality of beams of diffracted light produced by the polarization/diffraction grating.

Effect of the Invention

The present invention makes it possible to provide a birefringence measurement device and method capable of measuring a two-dimensional distribution of birefringence in a measurement target in real time and in detail using a simple configuration without a rotating mechanism.

MODES FOR CARRYING OUT THE INVENTION

Hereinafter, embodiments of a birefringence measurement device and method according to the present invention will be described with reference to the accompanying drawings.

First Embodiment

Figure 1:
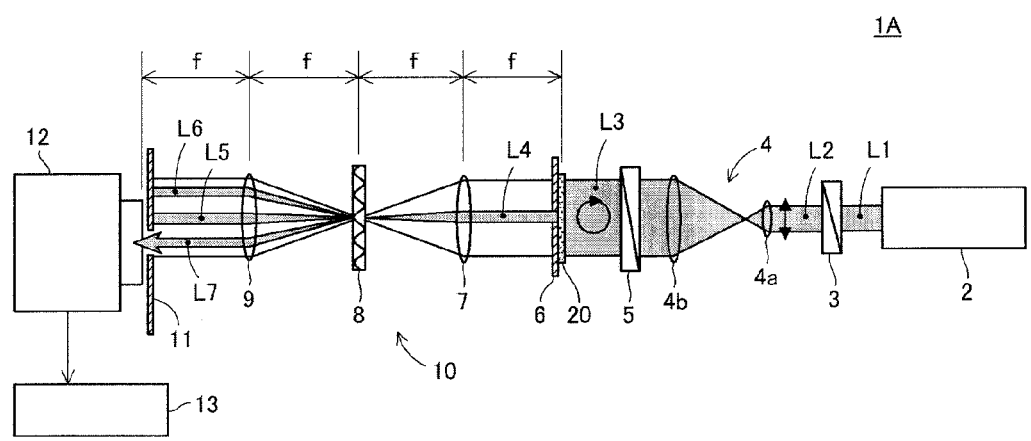
FIG. 1 is a schematic configuration diagram of a birefringence measurement device according to a first embodiment of the present invention.

FIG. 1 illustrates a birefringence measurement device 1A according to a first embodiment of the present invention. As shown in the figure, the birefringence measurement device 1A includes a laser light source 2 for generating laser light L1 with a specific polarization state, a polarizer 3 for creating linearly polarized light L2 from the laser light L1, a beam expander 4 for expanding the linearly polarized light L2, and a quarter-wave plate 5 for creating clockwise circularly polarized light L3 from the expanded linearly polarized light L2. The circularly polarized light L3 adjusted by the quarter-wave plate 5 is incident on a measurement target 20.

The laser light source 2 corresponds to "light flux generating means" of the present invention. The laser light source 2 emits laser light with a wavelength of 532 nm to the polarizer 3.

The beam expander 4 is constituted by a first lens 4a and a second lens 4b. As shown in FIG. 1, the second lens 4b has a larger diameter than the first lens 4a. The beam expander 4 expands the linearly polarized light L2 while keeping the polarization state thereof. The beam expander 4, along with the polarizer 3 and the quarter-wave plate 5, constitutes "light flux irradiating means" of the present invention.

The birefringence measurement device 1A further includes an imaging optical system 10 for forming an image from light L4 transmitted through the measurement target 20, a polarization/diffraction grating 8 disposed in a position within the imaging optical system 10, a CMOS camera 12 for generating a light-dark signal related to the brightness of the image formed by the imaging optical system 10, and a display 13 for outputting information regarding a phase difference δ between extraordinary and ordinary components of the transmitted light L4 (i.e., emission light) relative to the circularly polarized light L3 (i.e., incident light), the phase difference δ being determined on the basis of the light-dark signal.

The imaging optical system 10 includes a third lens 7 and a fourth lens 9, which are equal in diameter. All of the distances between the measurement target 20 and the third lens 7, between the third lens 7 and the polarization/diffraction grating 8, between the polarization/diffraction grating 8 and the fourth lens 9, and between the fourth lens 9 and a light detecting surface of the CMOS camera 12 are "f". That is, the imaging optical system 10 of the present embodiment is a 4f optical system.

The polarization/diffraction grating 8 produces a plurality of beams of diffracted light corresponding to the transmitted light L4 having passed through a first iris 6 with a size of 3 mm square. The beams include +1-order diffracted light L6 and −1-order diffracted light L7. The polarization/diffraction grating 8 also produces 0-order diffracted light L5 and ±2 or higher-order diffracted light, but the present embodiment does not utilize such light.

The CMOS camera 12 corresponds to "image pickup means" of the present invention. In the present embodiment, among the beams of diffracted light produced by the polarization/diffraction grating 8, only the −1-order diffracted light L7 having passed through a second iris 11 is incident on the light detecting portion of the CMOS camera 12. Thereafter, the CMOS camera 12 generates a light-dark signal related to the brightness of an image based on the −1-order diffracted light L7, and transmits the signal to the display 13. The light-dark signal may be transmitted upon an instruction by the operator or may be transmitted continuously at intervals of predetermined time (e.g., 1/30 of a second).

The display 13 corresponds to "output means" of the present invention. The display 13 detects the light-dark signal outputted by the CMOS camera 12, and displays an image representing a two-dimensional distribution of a phase difference δ between extraordinary and ordinary components of the transmitted light L4 on the basis of the relationship between a polarization state of the transmitted light L4, which is specified by the detected light-dark signal, and a known polarization state of the circularly polarized light L3 (in the present embodiment, clockwise circularly polarized light). The display 13 may include an arithmetic processing device involved in image generation.

In the case where the thickness d of the measurement target 20 is known, the two-dimensional distribution of the phase difference δ presented by the display 13 is equivalent to the two-dimensional distribution of birefringence Δn in the measurement target 20. On the other hand, in the case where the birefringence Δn in the measurement target 20 is known, the two-dimensional distribution of the phase difference δ presented by the display 13 is equivalent to the two-dimensional distribution of the thickness d of the measurement target 20.

Figure 2:
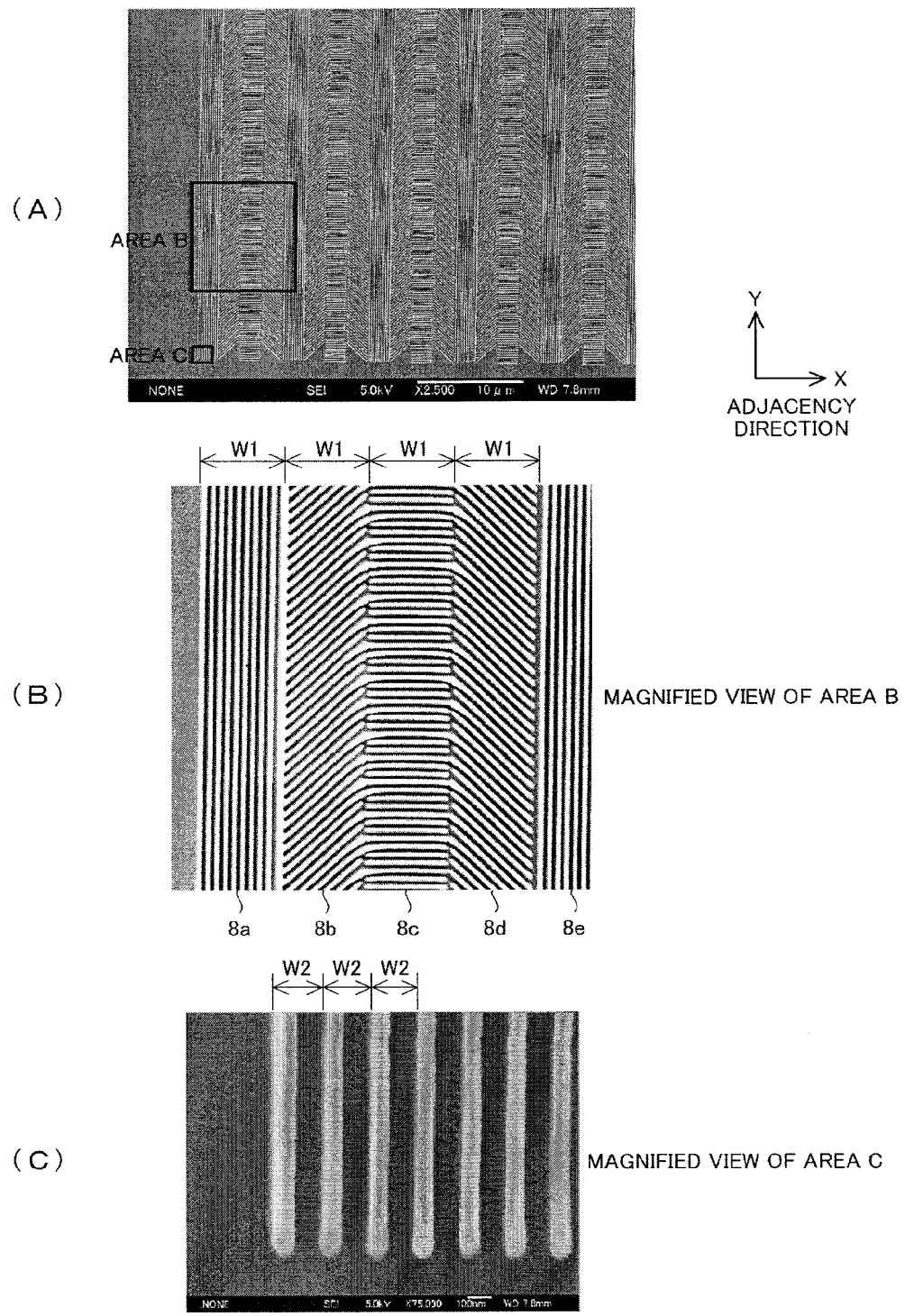
FIG. 2 provides scanning electron microscope (SEM) photos of the surface of a polarization/diffraction grating in the first embodiment.
Figure 3:
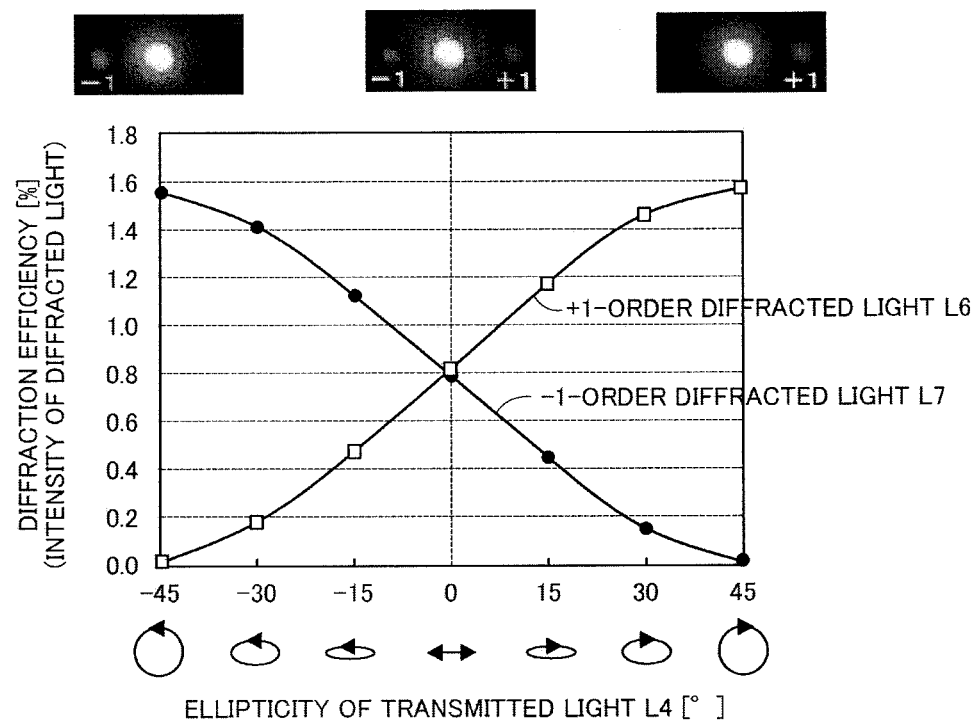
FIG. 3 is a graph showing the relationship between diffraction efficiency of +1-order diffracted light and −1-order diffracted light produced by the polarization/diffraction grating in the first embodiment and transmitted light incident on the polarization/diffraction grating.
Figure 4:
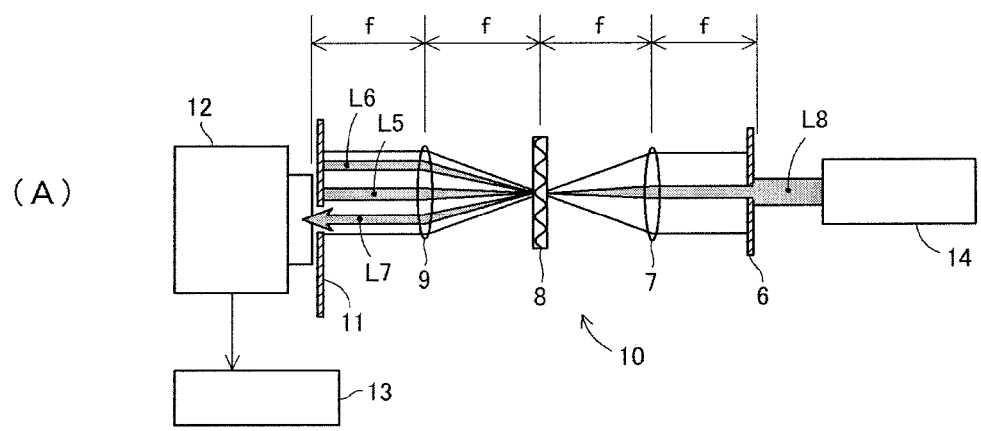
FIG. 4 provides diagrams describing the principle of measurement by the birefringence measurement device according to the first embodiment.
Figure 4:
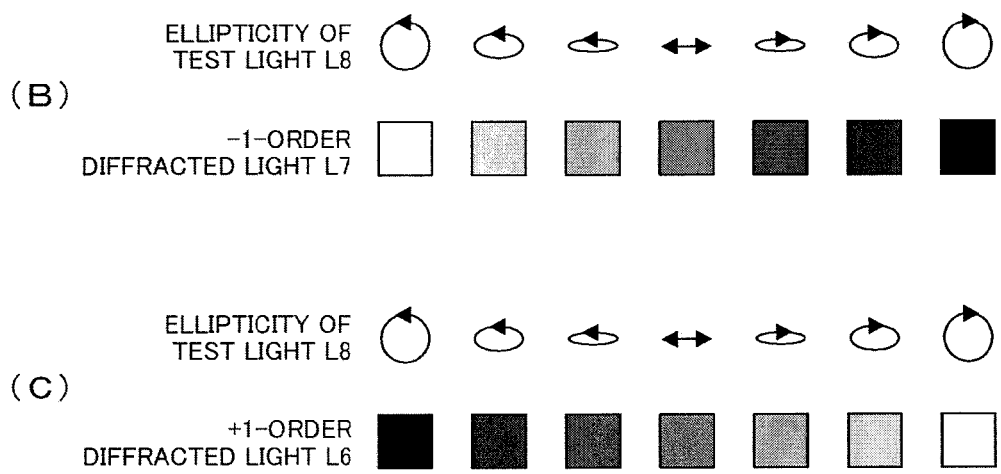

Referring next to FIGS. 2 to 4, the configuration of the polarization/diffraction grating 8 in the present embodiment and the principle of measuring the phase difference δ will be described in detail.

The polarization/diffraction grating 8 is a form birefringence/polarization/diffraction grating formed by arranging a plurality of grating units on one surface of a transparent resin plate having a thickness of about 10 µm by optical imprinting. As shown in FIGS. 2(A) and 2(B), the polarization/diffraction grating 8 has a periodic structure in X direction (hereinafter referred to as an "adjacency direction"). More specifically, the polarization/diffraction grating 8 has grating unit groups formed in series on its surface, each group consisting of a grating unit 8a in the form of a strip with a plurality of parallel grooves at 90° to the adjacency direction, a grating unit 8b in the form of a strip with a plurality of parallel grooves at 45° to the adjacency direction, a grating unit 8c in the form of a strip with a plurality of grooves parallel to the adjacency direction, and a grating unit 8d in the form of a strip with a plurality of parallel grooves at −45° to the adjacency direction. In other words, the polarization/diffraction grating 8 has formed thereon the grating unit 8a having a grating vector parallel to the adjacency direction, the grating unit 8b having a grating vector at −45° to the adjacency direction, the grating unit 8c having a grating vector at −90° to the adjacency direction, and the grating unit 8d having a grating vector at −135° to the adjacency direction.

In the present embodiment, each of the grating units 8a to 8d has a width W1 of 2000 nm in the adjacency direction.

To achieve the function of the polarization/diffraction grating rather than the function of a regular diffraction grating, the cycle W2 of the grooves in each of the grating units 8a to 8d (see FIG. 2(C)) is set to be sufficiently shorter than the wavelength of the laser light L1 to be generated by the laser light source 2. In the present embodiment, the groove cycle W2 is 200 nm. Moreover, in the present embodiment, the depth of the groove is 250 nm. In the case where the groove cycle W2 is set to be 0.6 times or more as much as the wavelength of the laser light L1 to be generated by the laser light source 2, the polarization/diffraction grating 8 does not function as a polarization/diffraction grating. Further, in view of S/N ratio, the grooves are preferably deep. For the grounds of setting the groove cycle W2 to be less than 0.6 times as much as the wavelength of the laser light L1, see Non-Patent Document 1 for detailed descriptions.

As described earlier, the polarization/diffraction grating 8 produces the +1-order diffracted light L6 and the −1-order diffracted light L7. As shown in FIG. 3, the +1-order diffracted light L6 (denoted by □) becomes weakest (i.e., darkest) where the light incident on the polarization/diffraction grating 8, i.e., the transmitted light L4 through the measurement target 20, is counterclockwise circularly polarized light, and becomes strongest (i.e., brightest) where the transmitted light L4 is clockwise circularly polarized light. On the other hand, the −1-order diffracted light L7 (denoted by ●) exhibits the opposite characteristic to the +1-order diffracted light L6, i.e., the −1-order diffracted light L7 becomes weakest (i.e., darkest) where the transmitted light L4 is clockwise circularly polarized light, and becomes strongest (i.e., brightest) where the transmitted light L4 is counterclockwise circularly polarized light. Note that the ellipticity of the transmitted light L4 on the horizontal axis of the graph shown in FIG. 3 is an ellipticity angle χ determined by the following equation.

$$\chi = \tan^{-1}\left(\frac{b}{a}\right) \quad \text{[Equation 3]}$$

Here, a is the length of the major axis of the ellipse, and b is the length of the minor axis of the ellipse.

In the case where various types of test light L8 with different polarization states are generated by a test light source 14 disposed in place of the laser light source 2 and other elements, as shown in FIG. 4(A), such that the light travels through the first iris 6 to be incident on the polarization/diffraction grating 8, the image that is obtained on the light detecting surface of the CMOS camera 12 becomes darkest where the test light L8 is clockwise circularly polarized light, and becomes brightest where the test light L8 is counterclockwise circularly polarized light (see FIG. 4(B)). Moreover, in the case where the position of the second iris 11 is shifted such that only the +1-order diffracted light L6 is incident on the CMOS camera 12, the image that is obtained on the light detecting surface of the CMOS camera 12 becomes brightest where the test light L8 is clockwise circularly polarized light, and becomes darkest where the test light L8 is counterclockwise circularly polarized light (see FIG. 4(C)).

In this manner, the birefringence measurement device 1A according to the first embodiment renders it possible to identify the polarization state of light (in FIG. 1, the transmitted light L4) incident on the polarization/diffraction grating 8 on the basis of the brightness of an image formed on the light detecting surface of the CMOS camera 12. In addition, on the basis of the relationship between the polarization of the transmitted light L4 and a known polarization state of the circularly polarized light L3 (in the present embodiment, clockwise circularly polarized light), at least a phase difference δ between extraordinary and ordinary components of the transmitted light L4 can be determined.

Furthermore, the brightness of the image formed on the light detecting surface of the CMOS camera 12 and the phase difference δ are in a one-to-one relationship. Therefore, by studying and tabulating the relationship therebetween in advance, the birefringence measurement device 1A according to the present embodiment renders it possible to determine the phase difference δ instantaneously on the basis of a light-dark signal.

Furthermore, as described earlier, the phase difference δ is the product of birefringence Δn in the measurement target 20 and the thickness d of the measurement target 20, and therefore, if the thickness d is known, the birefringence Δn in the measurement target 20 can be readily attained from the determined phase difference δ.

Next, examples of measurement by the birefringence measurement device 1A according to the first embodiment will be described in comparison with measurement by a polarizing microscope.

Measurement Example 1

Figure 5:
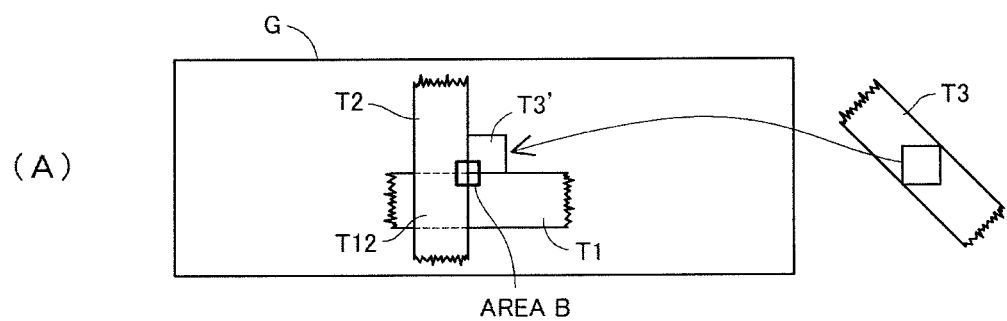
FIG. 5 provides representations related to Measurement Example 1 by the birefringence measurement device according to the first embodiment: (A) illustrating the structure of a measurement target used in Measurement Example 1, and (B) showing a measurement result for Measurement Example 1.
Figure 5:
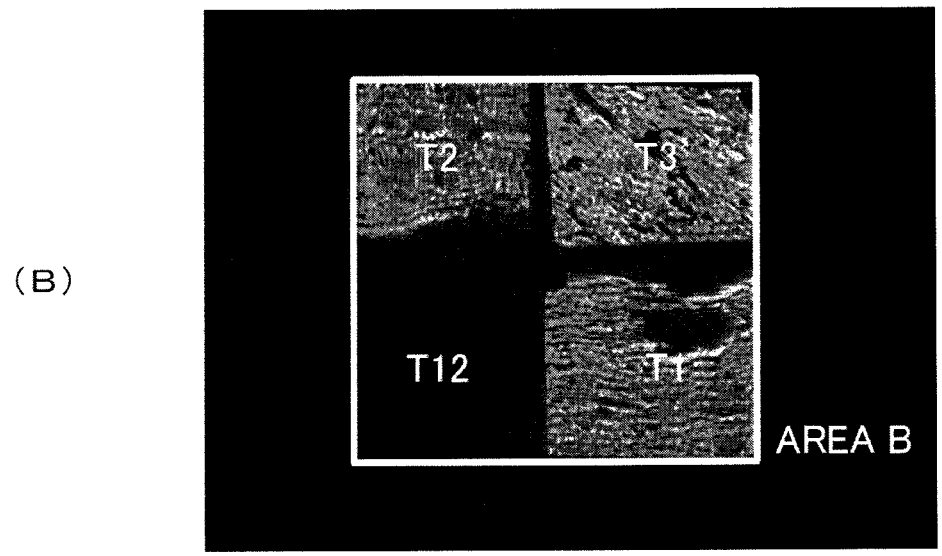

A commercially available cellophane tape was cut to prepare three strips T1, T2, and T3, the strip T1 was affixed to a glass slide G along a long side, the strip T2 was affixed so as to cross the strip T1 perpendicularly, and further, the strip T3 was affixed at 45° to the strip T1 such that a rectangular portion T3' of the strip T3 contacted both the strips T1 and T2, resulting in a measurement target shown in FIG. 5(A).

FIG. 5(B) provides a result of the birefringence measurement device 1A according to the first embodiment measuring an area B of the measurement target. Normally, the cellophane tape partially crystallizes during the process of manufacturing (more specifically, stretching), and there is a difference in birefringence Δn between crystallized and non-crystallized portions. This is the reason why there were differences in brightness among the strips T1, T2, and T3' the thickness of which was approximately uniform.

Furthermore, the strips T1, T2, and T3' differed from one another in distribution of birefringence Δn. This suggests that the measurement by the birefringence measurement device 1A according to the present embodiment renders it possible to identify the direction of stretching performed during manufacturing. As for an area T12 where the strips T1 and T2 overlapped, a completely different result from the strips T1, T2, and T3' was obtained. This suggests that in the area T12, the strips T1 and T2 were approximately equal in birefringence Δn and overlapped in a mutually perpendicular relationship, whereby a phase difference from circularly polarized light L3 (i.e., incident polarized light) was cancelled out, and substantial birefringence was not observed in the area T12.

Figure 6:
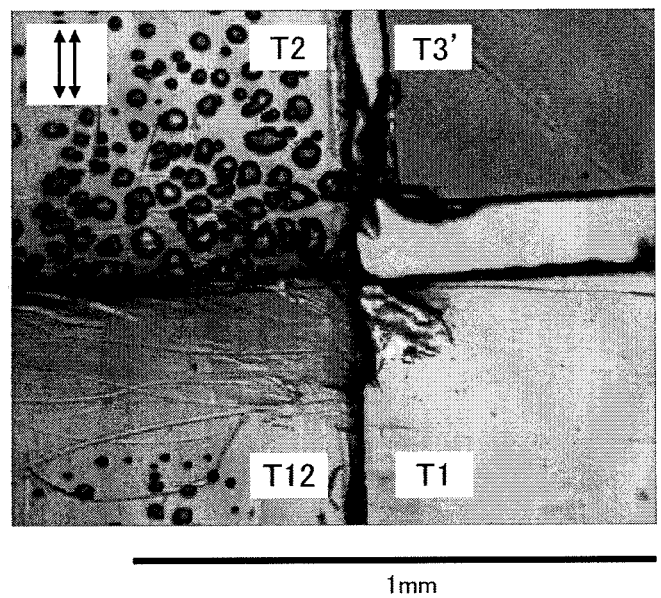
FIG. 6 provides a polarizing microscope photo of the measurement target in Measurement Example 1.

For comparison, the center of the area B was observed by a polarizing microscope using parallel Nicols, and the obtained result was as shown in FIG. 6. In FIG. 6, unlike in FIG. 5(B), there is no conspicuous difference found among the strip T1, the strip T2, and the area T12 where these strips overlap. This suggests that it is difficult for only a single observation by a polarizing microscope to identify the direction of stretching of a cellophane tape and to find portions different in thickness. Note that in FIG. 6, two parallel arrows indicate that the result was obtained by observation with the polarizer and the analyzer oriented in parallel, i.e., observation using parallel Nicols.

Measurement Example 2

Figure 7:
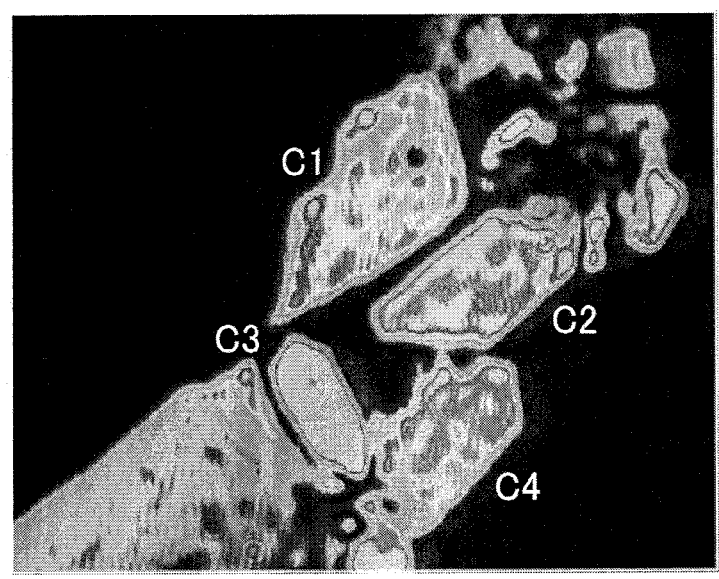
FIG. 7 is a representation showing a measurement result for Measurement Example 2 by the birefringence measurement device according to the first embodiment.

FIG. 7 provides a result of the birefringence measurement device 1A according to the first embodiment measuring sugar crystals as a measurement target. Sugar crystals are homogeneous, and therefore, birefringence Δn is constant. Accordingly, the brightness distribution in FIG. 7 can be said to represent crystal thickness d.

Figure 8:
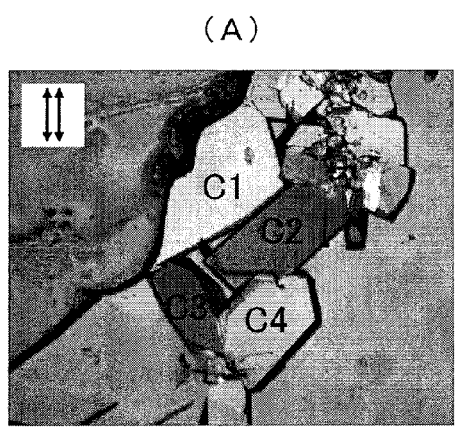
FIG. 8 provides polarizing microscope photos of a measurement target in Measurement Example 2.
Figure 8:
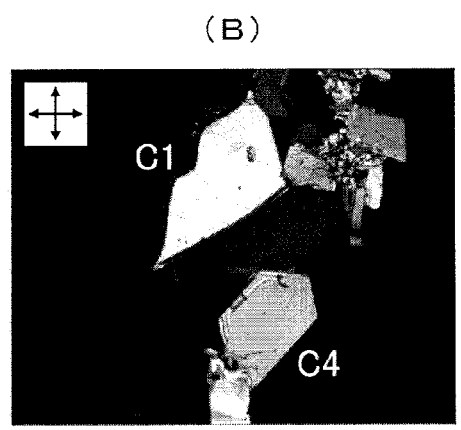
Figure 8:
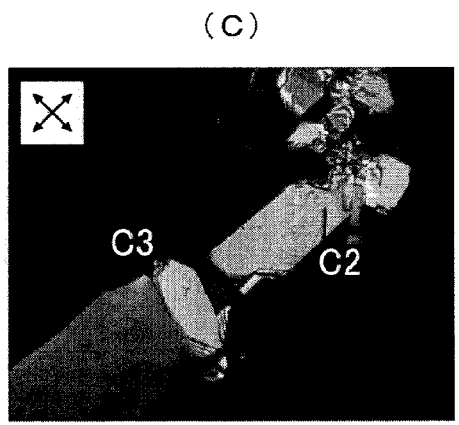
Figure 8:
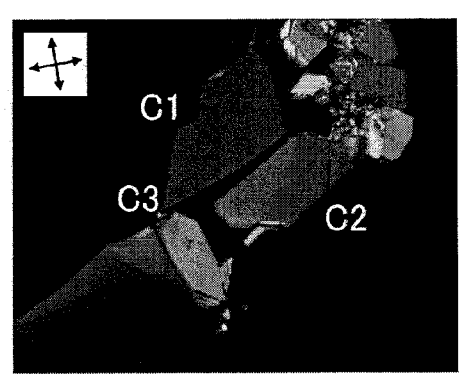

FIG. 8 provides observation results of the sugar crystals by the polarizing microscope using parallel Nicols ((A) in the figure) and crossed Nicols ((B) to (D) in the figure). As for the results of the crossed-Nicols observation where the polarizer and the analyzer were rotated relative to the sugar crystals, crystals C1 and C4 exhibited the highest brightness under the condition of (B) in the figure, and their brightness levels were about the same. As mentioned earlier, sugar crystals are constant in birefringence Δn, and therefore, both can be said to be close in thickness. However, to identify the relationship among all crystals in terms of thickness, the measurement with the polarizing microscope at least requires that observation and recording be performed in a crossed-Nicols arrangement while continuously rotating the sugar crystals, i.e., the measurement target, by 180°, and thereafter, data analysis be performed, resulting in a heavy workload and a requirement of rotating operation with high mechanical precision. Note that in FIG. 8, as in FIG. 6, two parallel arrows indicate that the result was obtained by observation using parallel Nicols. Moreover, in FIG. 8, two perpendicular arrows indicate that the result was obtained by observation with the polarizer and the analyzer oriented perpendicularly, i.e., observation using crossed Nicols.

[Ronchi Test]

Described next are the results of a Ronchi test performed using a device shown in FIG. 9(A) in order to evaluate the resolution of the birefringence measurement device 1A according to the first embodiment. Note that the device shown in FIG. 9(A) differs from the birefringence measurement device 1A in that a Ronchi grating 15 is disposed in place of the measurement target 20, the circularly polarized light L3 is adjusted to be elliptically polarized to a slight degree so that −1-order diffracted light L7 can be produced from light L4 passed through the birefringence-free Ronchi grating 15, and the imaging optical system 10 is a magnifying optical system (magnifying power: 2.1 times).

Figure 9:
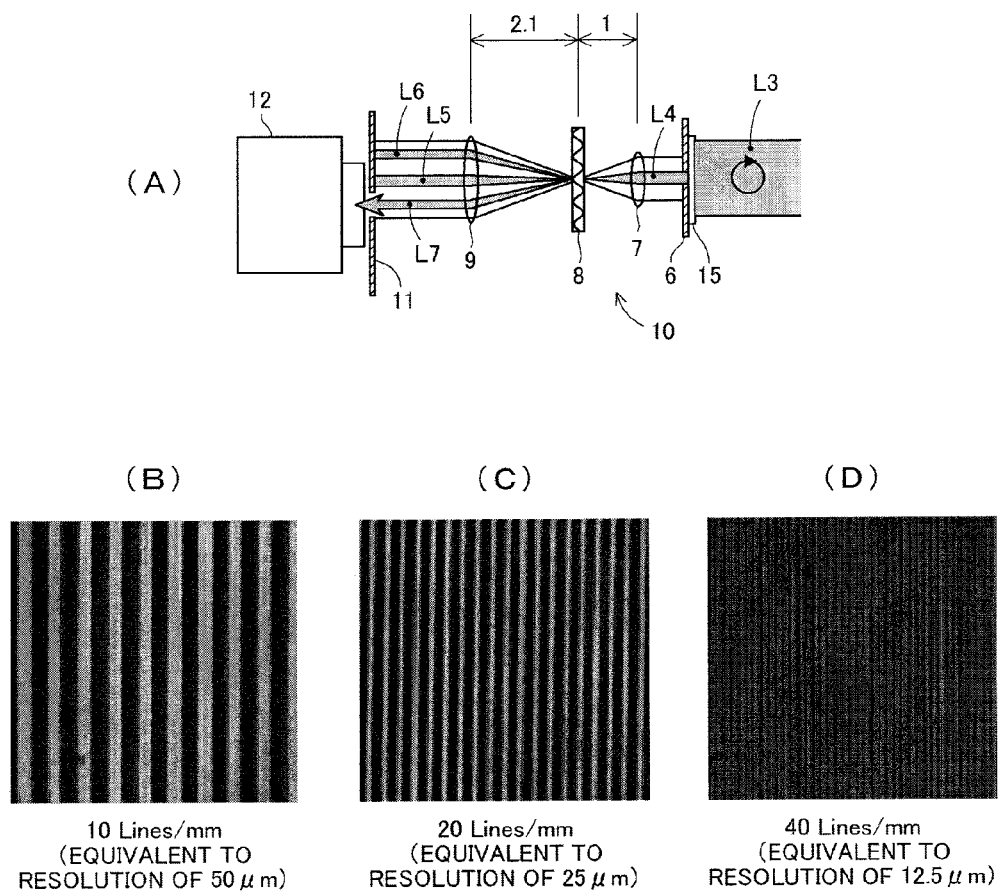
FIG. 9 provides representations related to a Ronchi test by the birefringence measurement device according to the first embodiment: (A) illustrating the configuration of the device used, and (B), (C), and (D) presenting determined brightness distribution images.

FIGS. 9(B) to 9(D) illustrate brightness distribution images obtained by the CMOS camera 12 where three types of Ronchi gratings 15 with 10 lines/mm, 20 lines/mm, and 40 lines/mm, respectively, were used. Even in the case where the 40 lines/mm Ronchi grating 15 having the narrowest stripe width were used, straight stripes were recognized clearly (see FIG. 9(D)). The results suggest that the device used in the evaluation had at least a resolution of 12.5 μm. That is, the results suggest that the birefringence measurement device 1A according to the first embodiment is suitable for micro measurement.

It should be noted that the above value 12.5 μm does not indicate the limit of the resolution of the birefringence measurement device 1A according to the first embodiment.

Second Embodiment

Figure 10:
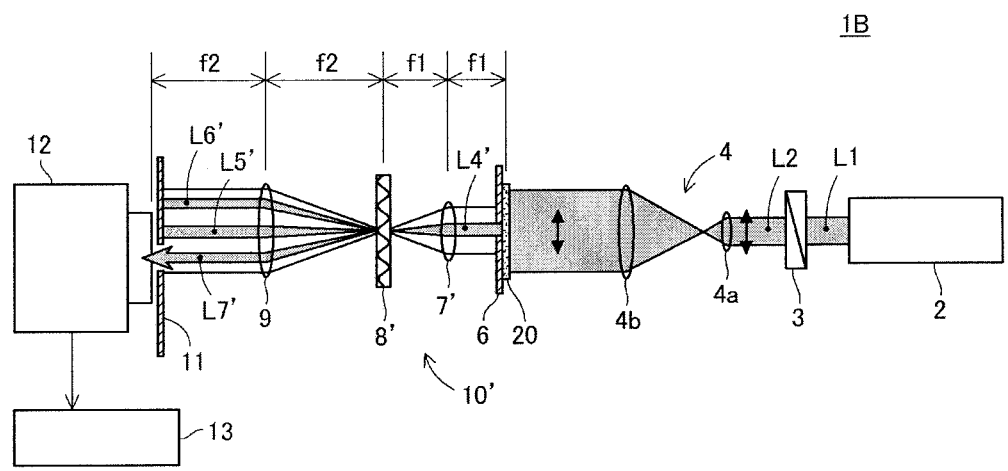
FIG. 10 is a schematic configuration diagram of a birefringence measurement device according to a second embodiment of the present invention.

FIG. 10 illustrates a birefringence measurement device 1B according to a second embodiment of the present invention. The birefringence measurement device 1B according to the present embodiment differs from the birefringence measurement device 1A in that the quarter-wave plate 5 is not included. Accordingly, in the birefringence measurement device 1B, linearly polarized light L2 expanded by the beam expander 4 is incident on the measurement target 20 without modification. As a result, in the present embodiment, transmitted light L4' and diffracted light L5', L6', and L7' different from counterparts thereof in the first embodiment are obtained.

Furthermore, the birefringence measurement device 1B differs from the birefringence measurement device 1A also in that an imaging optical system 10' is included. The imaging optical system 10' includes a third lens 7 and a fourth lens 9, which are different in diameter. Both the distance between the measurement target 20 and the third lens 7 and the distance between the third lens 7 and a polarization/diffraction grating 8' are "f1". On the other hand, both the distance between the polarization/diffraction grating 8' and the fourth lens 9 and the distance between the fourth lens 9 and the light detecting surface of the CMOS camera 12 are "f2" (where f2>f1).

Figure 11:
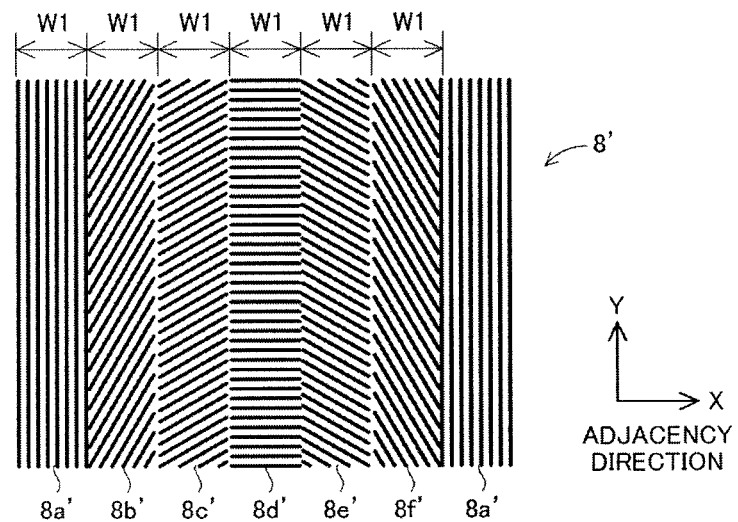
FIG. 11 is a surface view illustrating the configuration of a polarization/diffraction grating in the second embodiment FIG. 12 provides representations showing measurement results for Measurement Example 3 by the birefringence measurement device according to the second embodiment.

The birefringence measurement device 1B differs from the birefringence measurement device 1A also in that the polarization/diffraction grating 8' is included. The polarization/diffraction grating 8' is a form birefringence/polarization/diffraction grating manufactured in the same manner as the polarization/diffraction grating 8. The polarization/diffraction grating 8' has a periodic structure in X direction (adjacency direction), as shown in FIG. 11. More specifically, the polarization/diffraction grating 8' has grating units formed in series on its surface, including a grating unit 8a' in the form of a strip with a plurality of parallel grooves at 90° to the adjacency direction, a grating unit 8b' in the form of a strip with a plurality of parallel grooves at 600 to the adjacency direction, a grating unit Sc' in the form of a strip with a plurality of parallel grooves at 30° to the adjacency direction, a grating unit 8d' in the form of a strip with a plurality of grooves parallel to the adjacency direction, a grating unit 8e' in the form of a strip with a plurality of parallel grooves at −30° to the adjacency direction, and a grating unit 8f in the form of a strip with a plurality of parallel grooves at −60° to the adjacency direction. In other words, the polarization/diffraction grating 8' has formed thereon the grating unit 8a' having a grating vector parallel to the adjacency direction, the grating unit 8b' having a grating vector at −30° to the adjacency direction, the grating unit 8c' having a grating vector at −60° to the adjacency direction, the grating unit 8d' having a grating vector at −90° to the adjacency direction, the grating unit 8e' having a grating vector at −120° to the adjacency direction, and the grating unit 8f' having a grating vector at −150° to the adjacency direction.

The grating units 8a' to 8f' in the present embodiment are the same as the grating units in the first embodiment in terms of the width W1 in the adjacency direction, the groove cycle, and the groove depth.

As with the polarization/diffraction grating 8, the polarization/diffraction grating 8' produces +1-order diffracted light L6' and −1-order diffracted light L7'. However, changes in groove orientation (grating vector) at the boundaries of the grating units are moderate compared to the polarization/diffraction grating 8, so that the +1-order diffracted light L6' and the −1-order diffracted light L7' produced by the polarization/diffraction grating 8' are higher in diffraction efficiency (intensity) than the +1-order diffracted light L6 and the −1-order diffracted light L7 produced by the polarization/diffraction grating 8. Accordingly, by using the polarization/diffraction grating 8', it is rendered possible to perform a measurement with a higher S/N ratio.

In the birefringence measurement device 1B according to the present embodiment, the linearly polarized light L2 is incident on the measurement target 20, as mentioned earlier. Accordingly, in the case where no birefringence occurs in the measurement target 20, i.e., in the case where the transmitted light L4' incident on the polarization/diffraction grating 8' is linearly polarized light, the −1-order diffracted light L7' has about the middle level of brightness (see FIG. 4(B)). In addition, in the case where birefringence occurs in the measurement target 20, the −1-order diffracted light L7' becomes brightest where the transmitted light L4' is counterclockwise circularly polarized light, and the −1-order diffracted light L7' becomes darkest where the transmitted light L4' is clockwise circularly polarized light.

The CMOS camera 12 generates a light-dark signal related to the brightness of an image based on the −1-order diffracted light L7', and transmits the signal to the display 13. Then, on the basis of the relationship between a polarization state of the transmitted light L4' specified by the detected light-dark signal and a known polarization of the linearly polarized light L2, the display 13 presents an image representing a two-dimensional distribution of a phase difference δ between extraordinary and ordinary components of the transmitted light L4'.

Described next is Measurement Example 3 by a device similar to the birefringence measurement device 1B according to the second embodiment. The device used in Measurement Example 3 differs from the birefringence measurement device 1B in that circularly polarized light is incident on the measurement target 20. To allow circularly polarized light to be incident on the measurement target 20, it is simply required to use, for example, the quarter-wave plate 5 (see FIG. 1).

Measurement Example 3

Figure 12:
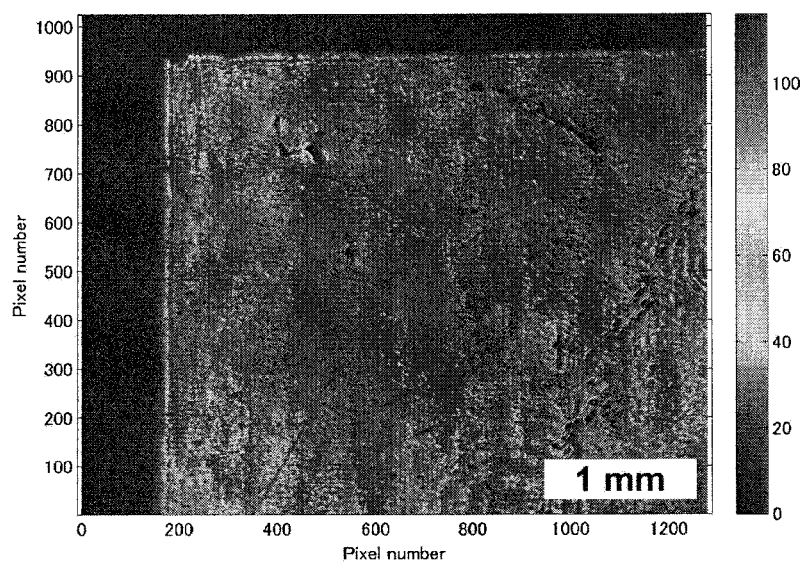
Figure 12:
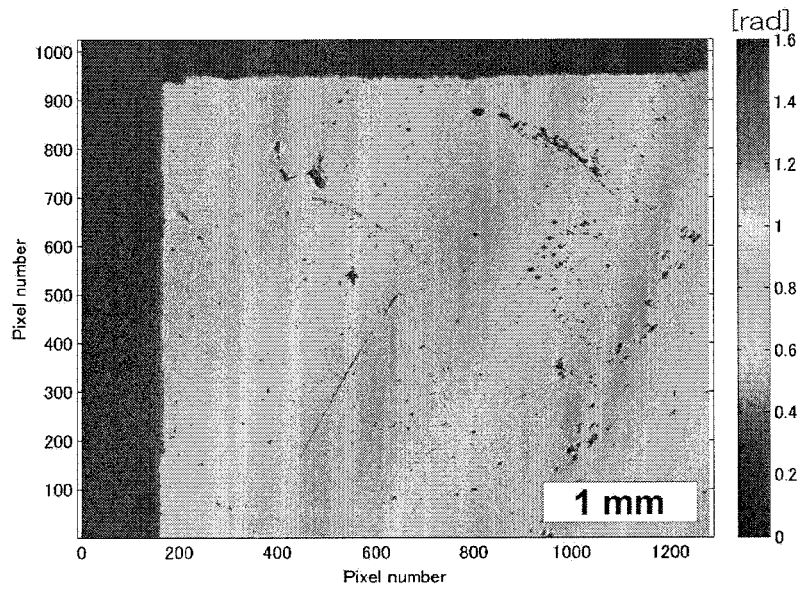

In the present measurement example, the measurement target is a polyethylene film having a thickness d of 20 μm. FIG. 12(A) is a brightness distribution image based on a light-dark signal outputted by the CMOS camera 12, and FIG. 12(B) is a phase difference distribution image obtained by converting brightness in the brightness distribution image into phase difference δ. Changes in phase difference δ due to the presence of scratches and compositional defects can be found more clearly in the phase difference distribution image shown in FIG. 12(B) than in the brightness distribution image shown in FIG. 12(A).

It should be noted that if the polyethylene film is scratched, the scratched area is dented, and its peripheral portion rises, resulting in a change in thickness d. Moreover, in the case where there is any compositional defect, such a defected area exhibits a different characteristic of birefringence Δn compared to other areas. From the phase difference distribution image shown in FIG. 12(B), changes in thickness d or birefringence Δn can be confirmed through changes in phase difference δ.

Third Embodiment

Figure 13:
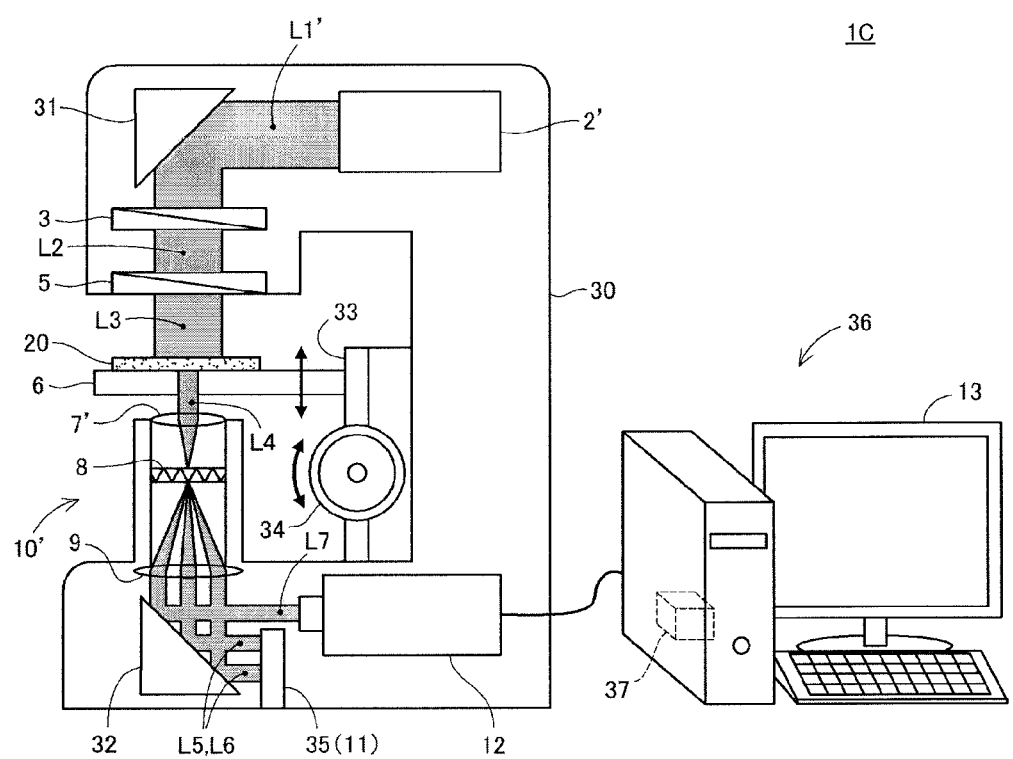
FIG. 13 is a schematic configuration diagram of a birefringence measurement device according to a third embodiment of the present invention.

FIG. 13 illustrates a desktop birefringence measurement device 1C according to a third embodiment of the present invention. The birefringence measurement device 1C differs from the birefringence measurement device 1A according to the first embodiment mainly in that a space-saving light source 2' integrated with a simplified beam expander is used and an imaging optical system 10' is included in place of the imaging optical system 10, and the entire device excluding the display 13 is accommodated in a housing 30 for easy handling.

As shown in FIG. 13, the birefringence measurement device 1C includes a light source 2' for generating light flux L1' in a specific polarization state, a first reflector 31 for changing the travel direction of the light flux L1' from horizontal to vertical, a polarizer 3 for creating linearly polarized light L2 from the vertically traveling light flux L1', a quarter-wave plate 5 for creating clockwise circularly polarized light L3 from the linearly polarized light L2, and a first iris 6 doubling as a stage. The circularly polarized light L3 adjusted by the quarter-wave plate 5 is incident on a measurement target 20 placed on the first iris 6. The first iris 6 preferably includes a mechanism for securing the measurement target 20. Moreover, the light source 2' is a laser diode.

The birefringence measurement device 1C further includes an imaging optical system 10' (7' and 9) for forming an image from light L4 transmitted through the measurement target 20, a combination of a polarization/diffraction grating 8 and a second reflector 32, both of which are disposed in some positions within the imaging optical system 10', and a CMOS camera 12 for generating a light-dark signal related to the brightness of the image formed by the imaging optical system 10'. The second reflector 32 changes the travel direction of diffracted light L5, L6, and L7 from vertical to horizontal.

In the present embodiment, as in the first embodiment, among the three beams of diffracted light L5, L6, and L7, only the −1-order diffracted light L7 is incident on the light detecting portion of the CMOS camera 12. The other two beams of diffracted light L5 and L6 are blocked by a light shielding plate 35 (corresponding to the second iris 11 in the first embodiment).

The birefringence measurement device 1C further includes a wall surface 33 for supporting an edge of the first iris 6, and an adjustment knob 34 provided in its vicinity. When the adjustment knob 34 is turned by the operator, the first iris 6 moves up or down a very short distance corresponding to the amount of turn. This cancels out a positional deviation of the measurement target 20 relative to a front focal point of the third lens 7', thereby adjusting the focus of the imaging optical system 10'. On the other hand, the third lens 7, the fourth lens 9, the polarization/diffraction grating 8, the second reflector 32, and the CMOS camera 12 are fixed at appropriate positions within the housing 30. In particular, the polarization/diffraction grating 8 is fixed at a rear focal point of the third lens 7'. Accordingly, upon measurement, the operator is not required to adjust the positions of these elements.

The birefringence measurement device 1C is further provided with a computer 36 including the display 13. The computer 36 incorporates an arithmetic processing device 37 for generating a two-dimensional distribution image for phase difference δ on the basis of a light-dark signal outputted by the CMOS camera 12. In addition, the display 13 presents the two-dimensional distribution image for phase difference δ generated by the arithmetic processing device 37.

[Variants]

While the embodiments of the birefringence measurement device and method according to the present invention have been described above, the present invention is not limited to these configurations.

For example, the "light flux generating means" of the present invention is not limited to either the laser light source 2, which outputs laser light having a wavelength of 532 nm, or the light source 2', which is a laser diode, and the "light flux generating means" may be a light source, such as a lamp, which is capable of generating non-polarized light flux.

The "light flux irradiating means" of the present invention can be suitably reconfigured so long as the light flux generated by the "light flux generating means" can be in a predetermined polarization state and the measurement target 20 can be irradiated with such flux. The polarization state of the light flux incident on the measurement target 20 may be a known elliptically polarized state. Moreover, the beam expander 4 can be omitted.

The "imaging optical system" of the present invention can be suitably reconfigured so long as an image based on light L4 (L4') transmitted through the measurement target 20 can be formed on the light detecting surface of the CMOS camera 12 serving as the "image pickup means".

The "image pickup means" of the present invention may be an arbitrary device or element capable of generating a light-dark signal related to the brightness of an image formed on the light detecting surface.

The "output means" of the present invention may be an arbitrary device or element capable of outputting information regarding a phase difference δ (or birefringence Δn or a thickness d) determined on the basis of a detected light-dark signal. The information regarding a phase difference δ (or birefringence Δn or a thickness d) may be a two-dimensional image or numerical data.

The "polarization/diffraction grating" of the present invention may be a form birefringence/polarization/diffraction grating formed from a transparent quartz plate by an arbitrary method or may be a polarization/diffraction grating which utilizes molecular orientation. Moreover, the difference in grating vector orientation between adjacent grating units is not limited to either 45° or 30°, and can be set to any angle of 45° or less. In view of S/N ratio, the difference in grating vector orientation is preferably small. In the case where a polarization/diffraction grating which utilizes molecular orientation is used, attention needs to be paid because molecular disorientation might occur due to a temperature rise by laser light irradiation.

The "image pickup means" of the present invention may generate a light-dark signal based on +1-order diffracted light L6 (L6'). Moreover, the "image pickup means" may generate a light-dark signal on the basis of both −1-order diffracted light L7 (L7') and +1-order diffracted light L6 (L6'. By using both of the two beams of diffracted light L7 (L7') and L6 (L6') opposite in characteristic, it is rendered possible to perform a noise-resistant measurement.

The "output means" of the present invention may determine a phase difference δ by the equation below on the basis of a diffracted light intensity I specified by a light-dark signal and a maximum diffracted light intensity $I_{max}$ measured in advance.

$$\delta = 2\sin^{-1}\left(\sqrt{\frac{I}{I_{max}}}\right) - \frac{\pi}{4} \qquad \text{[Equation 4]}$$

Note that in the case where −1-order diffracted light L7 (L7') is used, a diffracted light intensity I measured by the CMOS camera 12 upon incidence of counterclockwise circularly polarized light L8 generated by the test light source 14 or suchlike on the polarization/diffraction grating 8 is used as a maximum diffracted light intensity $I_{max}$ (see FIG. 4(B)). Moreover, in the case where +1-order diffracted light L6 (L6') is used, a diffracted light intensity I measured by the CMOS camera 12 upon incidence of clockwise circularly polarized light L8 generated by the test light source 14 or suchlike on the polarization/diffraction grating 8 is used as a maximum diffracted light intensity $I_{max}$ (see FIG. 4(C)).

Figure 14:
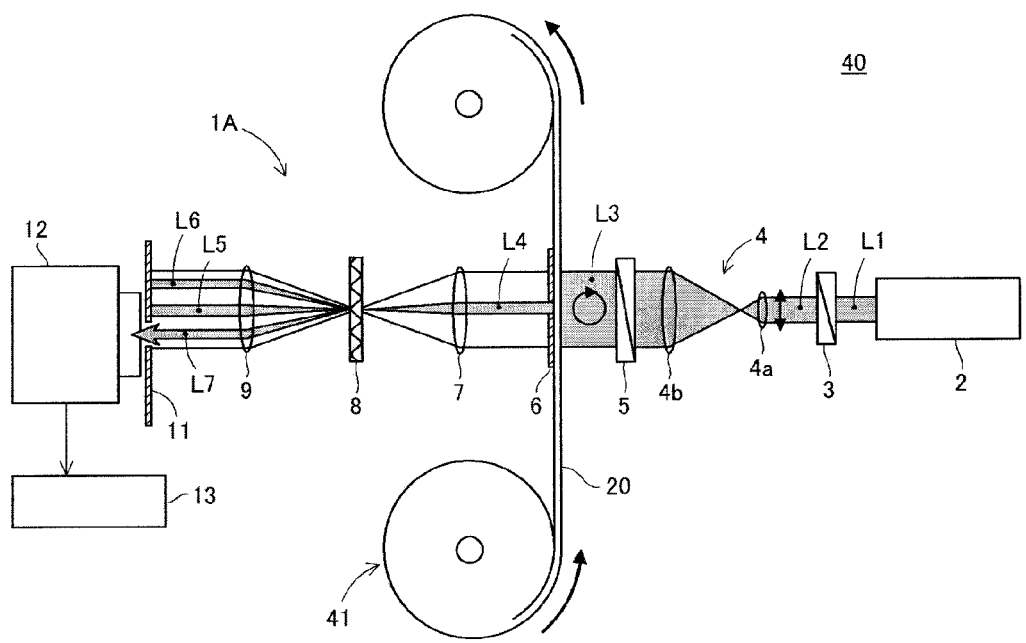
FIG. 14 is a schematic configuration diagram of a film inspection device including a birefringence measurement device according to the present invention.
Figure 15:
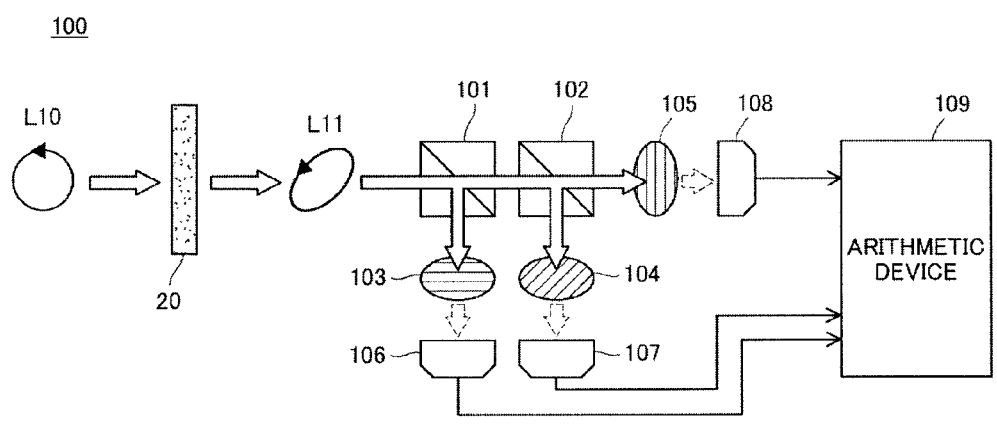
FIG. 15 is a schematic configuration diagram of a conventional birefringence measurement device.
Figure 16:
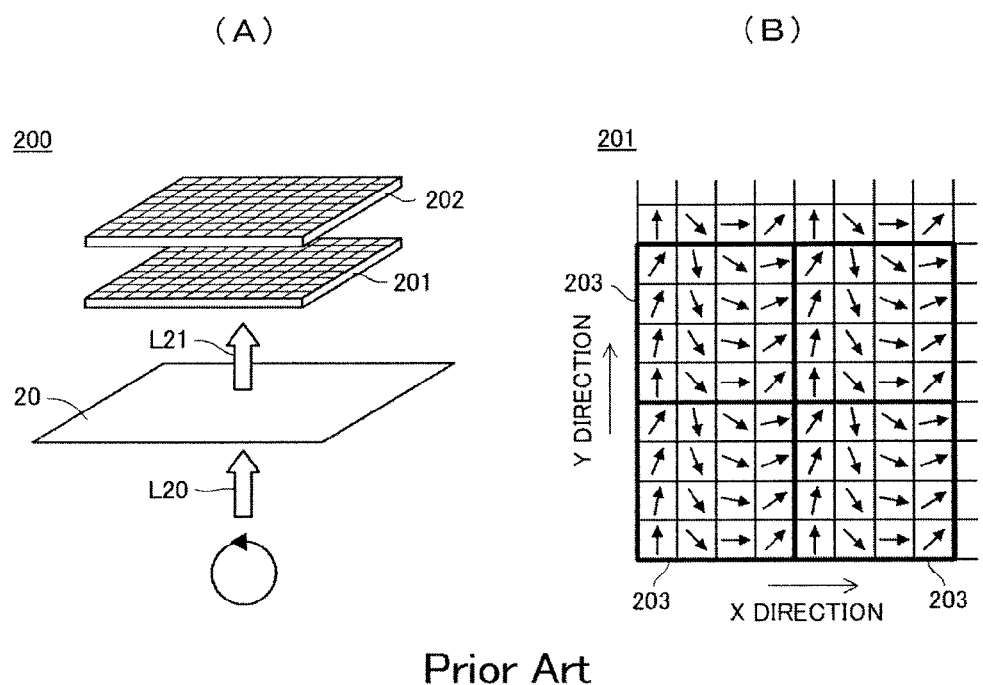
FIG. 16 is a schematic configuration diagram of another conventional birefringence measurement device.

Furthermore, the birefringence measurement device according to the present invention can be utilized as a film inspection device for detecting abnormal birefringence in mass-produced films. In this case, as shown in FIG. 14, the film inspection device 40 includes a birefringence measurement device according to the present invention (e.g., a birefringence measurement device 1A) and a film supply mechanism 41 for continuously supplying a film to be passed through a predetermined position as a measurement medium 20. To completely inspect the entire area of the film, the CMOS camera 12 generates a light-dark signal per period of time corresponding to the speed of film supply.

The film inspection device 40 may include a plurality of birefringence measurement devices (e.g., birefringence measurement devices 1A). For example, by arranging birefringence measurement devices 1A in a direction perpendicular to the direction in which the film is supplied (i.e., in the direction of film width) such that the birefringence measurement devices 1A are involved in inspecting different areas of the film, it is rendered possible to inspect a wide film without increasing inspection time.

INDUSTRIAL APPLICABILITY

The present invention can be utilized for inspecting and evaluating various birefringent media. The present invention is useful particularly for continuous and fast inspection of various mass-produced films (e.g., transparent raw films, coating materials, and functional films) to determine whether there is any defect in composition or appearance.

DESCRIPTION OF THE REFERENCE CHARACTERS 1A, 1B, 1C birefringence measurement device
2 laser light source 2' light source
3 polarizer
4 beam expander
4a first lens
4b second lens
5 quarter-wave plate
6 first iris
7, 7 third lens
8, 8' polarization/diffraction grating
9 fourth lens
10, 10' imaging optical system
11 second iris
12 CMOS camera
13 display
14 test light source
15 Ronchi grating
20 measurement target (birefringent medium)
30 housing
31 first reflector
32 second reflector
33 wall surface
34 adjustment knob
35 light shielding plate
36 computer
37 arithmetic processing device
40 film inspection device
41 film supply mechanism
L1 laser light
L1' light flux
L2 linearly polarized light
L3 circularly polarized light
L4, L4' transmitted light
L5, L5' 0-order diffracted light
L6, L6' +1-order diffracted light
L7, L7' −1-order diffracted light

The invention claimed is:

1. A birefringence measurement device comprising:
light flux generating means for generating light flux;
light flux irradiating means for irradiating a measurement target with the light flux in a predetermined polarization state;
an imaging optical system for forming an image from light flux transmitted through the measurement target;
a polarization/diffraction grating disposed in a position within the imaging optical system;
image pickup means for generating a light-dark signal related to brightness of the image formed by the imaging optical system; and
output means for outputting information regarding a phase difference for the light flux transmitted through the measurement target, the phase difference resulting from the transmission through the measurement target and being determined on the basis of the light-dark signal, wherein,
the image pickup means generates the light-dark signal for an image based on at least one of a plurality of beams of diffracted light produced by the polarization/diffraction grating.

2. The birefringence measurement device according to claim 1, wherein the light flux incident on the measurement target is circularly polarized light.

3. The birefringence measurement device according to claim 2, wherein the image pickup means generates the light-dark signal for an image based on the beam of diffracted light produced by the polarization/diffraction grating, the beam being either +1- or −1-order diffracted light and becoming darkest when the light flux transmitted through the measurement target has the same circular polarization as circularly polarized light incident on the measurement target and becoming brightest when the light flux transmitted through the measurement target has opposite circular polarization to the circularly polarized light incident on the measurement target.

4. The birefringence measurement device according to claim 1, wherein the polarization/diffraction grating is a form birefringence/polarization/diffraction grating made from a quartz plate or a transparent resin plate.

5. The birefringence measurement device according to claim 4, wherein,
the polarization/diffraction grating includes a plurality of grating units arranged in an adjacency direction,
each of the grating units is a one-dimensional strip grating, and
each adjacent pair of the grating units differs in grating vector orientation so as to form a periodic structure in the adjacency direction.

6. The birefringence measurement device according to claim 5, wherein the cycle of the strip gratings is shorter than 0.6 times the wavelength of the light flux generated by the light flux generating means.

7. The birefringence measurement device according to claim 1, wherein,
the imaging optical system is a 4f optical system, and
the polarization/diffraction grating is disposed halfway between the measurement target and the image pickup means.

8. A film inspection device comprising a birefringence measurement device of claim 1 and being used for detecting abnormal birefringence in a film serving as the measurement target.

9. A birefringence measurement method comprising:
a light flux generating step for generating light flux;
a light flux irradiating step for irradiating a measurement target with the light flux in a predetermined polarization state;
an image forming step for forming an image from light flux transmitted through the measurement target by means of a polarization/diffraction grating;
a signal generating step for generating a light-dark signal related to brightness of the image formed in the image forming step; and
an output step for outputting information regarding a phase difference for the light flux transmitted through the measurement target, the phase difference resulting from the transmission through the measurement target and being determined on the basis of the light-dark signal, wherein,
in the signal generating step, the light-dark signal is generated for an image based on at least one of a plurality of beams of diffracted light produced by the polarization/diffraction grating.

10. A film inspection method detecting abnormal birefringence in a film serving as the measurement target by the birefringence measurement method of claim 9.

* * * * *